| United States Patent [19] | [11] | 4,217,417 |
|---|---|---|
| Smith | [45] | Aug. 12, 1980 |

[54] RESIN CHELATES

[75] Inventor: Robert L. Smith, Hounslow, England

[73] Assignee: Diamond Shamrock (Polymers) Limited, United Kingdom

[21] Appl. No.: 900,359

[22] Filed: Apr. 26, 1978

[30] Foreign Application Priority Data

Apr. 29, 1977 [GB] United Kingdom ............... 17984/77

[51] Int. Cl.$^2$ ....................... C12N 11/08; C12P 19/20
[52] U.S. Cl. .................................... 435/180; 435/181; 435/177; 435/96; 71/64 F; 71/DIG. 2
[58] Field of Search .................. 195/63, 68, DIG. 11; 435/177, 180, 181

[56] References Cited

U.S. PATENT DOCUMENTS

| 3,912,593 | 10/1975 | Barker et al. ........................ 195/63 X |
| 4,038,140 | 7/1977 | Jaworek et al. ........................ 195/63 |
| 4,115,198 | 9/1978 | Coughlin et al. ........................ 195/63 |

FOREIGN PATENT DOCUMENTS

| 1346631 | 2/1974 | United Kingdom . |
| 1352739 | 5/1974 | United Kingdom . |
| 1353317 | 5/1974 | United Kingdom . |
| 1388580 | 3/1975 | United Kingdom . |
| 1454850 | 11/1976 | United Kingdom . |

*Primary Examiner*—Lionel M. Shapiro
*Attorney, Agent, or Firm*—William A. Skinner

[57] ABSTRACT

Complexes of metals with chelating resins are described. In the principal embodiment the complex is a complex of a resin, an enzyme and a metal that is in non-ionic form and that is chelated by the resin and the enzyme. Such material is of particular value for converting dextrin to glucose. In another embodiment a solid agricultural composition is formed comprising a complex of an agriculturally acceptable trace metal chelated by a chelating resin and finely divided solid carrier.

6 Claims, No Drawings

RESIN CHELATES

The use of enzymes as catalysts for organic reactions is of growing importance because enzymatic action is fast and specific (no unwanted by-products to separate), the reactions can be conducted under nonhazardous conditions, need temperatures well below the boiling point of water, and do not require that the apparatus should resist corrosion or withstand pressures significantly above atmospheric conditions.

The main disadvantage associated with known enzyme systems has been that the enzymatic process must be conducted as a batch manufacture. The enzyme used must be separated and separated enzyme is generally of no further use. In the chemical industry in general there has been an ever-increasing desire to use heterogeneous phase systems with catalysts instead of homogeneous ones since they are readily separated and continuous processes become more feasible. Thus insolubilised enzyme systems have become of great interest.

Various enzymes have been chemically linked to substrates and especially to crosslinked polyacrylamide matrices. Various coupling agents and reactions are used to attach the particular enzyme to the substrate. The choice is limited by whether the enzyme will withstand the chemical reactions involved and how much may be destroyed or inactivated in the process.

It is known that if surfaces of cellulose, glass or nylon are washed with aqueous solutions of transition metal salts such as $TiCl_4$, $TiCl_3$, $SnCl_4$, $ZrCl_4$, $VCl_3$, $FeCl_3$ or $FeCl_2$, then washed free of the salt solution, and the treated surface is then contacted with solutions of various enzymes and then washed free of the enzyme still in solution, it is found that enzyme is attached to the surface, as is shown by activity in its particular enzymatic reaction. Enzymes which have been so bonded include amyloglucosidase, alpha-amylase, trypsin, glucose oxidase and invertase. However, it has proved difficult to turn this knowledge into practical effect as the effective linkage between enzymes and glass, nylon or cellulose is weak and, in the course of continuous operation, the linkages are broken leading to a loss of efficiency to a degree which is unacceptable.

Chelating resins have been known for many years and have been used industrially, for example in hydrometallurgy and in effluent treatment, and in particular in the final treatment of radioactive effluents. Chelating resins can be manufactured in a manner similar to ion-exchange resins but differ from them in that the pendant groups attached to the matrix are neither simple acidic groups such as sulphonic or carboxylic acid groups nor simple basic groups such as tertiary or quaternary amino groups. Chelating resins include groups which can hold a metal by co-ordinate or chelate bonds. The metal is held in non-ionic form and not in the loose manner of counter ions which is the method of retention by conventional ion-exchange resins.

Chelating resins have been used essentially as metal collectors, but they have not been used in connection with the insolubilisation of enzymes.

According to the present invention, an enzymatically active enzyme-support complex comprises a chelating resin; an enzyme; and a metal in non-ionic form chelated by the resin and by the enzyme.

This invention provides enzymes fixed on a suitable substrate which can retain the enzyme effectively in use, while avoiding the chemical reactions which lead to permanent covalent bonds between substrate and enzyme. The invention depends on anchorage by co-ordination bonds or attraction but in a manner which is superior to the inadequate bonding achieved in earlier methods, described above.

The complexes of this invention are apparently mixed chelates i.e. the metal is held to the resin by chelation using only some of its co-ordination positions.

By the term "enzymatically active" we mean that the complexes of the invention contain the enzyme in a form in which it can catalyse its specific reaction. Some enzymes are thus excluded from the scope of this invention, such as those which lose their activity by chelating a metal. In general, the enzymes relevant to this invention have amino acid groups which link to the unfilled co-ordination positions of the metal retained on the resin. There are some enzymes which derive their activity from the presence of a chelated metal. Such enzymes lie outside the scope of this invention owing to the fact that, in the novel complexes, some of the metal co-ordination positions are occupied by the chelating resin. Further, enzymes whose activity is destroyed by the presence of a soluble chelating agent such as ethylenediaminetetraacetic acid (EDTA) are not suitable for use in the present invention. Although they would be held by a chelating resin their activity would be suppressed by the resin in the same manner in which it is suppressed by a soluble chelating agent. However, only a few enzymes depend for their activity on a chelated metal while there are many which chelate metals in solution by virtue of the amino acid groups which are present in their structure but which are not essential to their activity as enzymes. Our invention is concerned with those enzymes which do chelate metals but in which the chelation of a metal is not relevant to their enzymatic activity.

Although many chelating resins have been reported in connection with theoretical studies or industrial uses, we believe that most will be satisfactory for use as supports in this invention. The preferred resins for use in this invention are of the type described as macroporous or macroreticular, and are preferably crosslinked polystyrene or crosslinked polyacrylamides. Such resins can be prepared in macroreticular form in the manner known for the manufacture of ion-exchange matrices. The preferred pendant chelating groups are methyleneaminodiacetic acid groups, e.g. —$CH_2N(CH_2COOH)_2$, groups, although methyleneaminoacetic groups may also be present depending on the process of manufacture. However, other groups suggested for chelating resins and known soluble chelating agents, where they can be attached without detriment to their action to suitable matrices, may be suitable. One such example of a pendant group allied to an important class of soluble chelating agents is methyleneaminodi(methylphosphonic acid).

The most preferred resins for use in the invention are macroreticular and are those (a) based on polystyrene crosslinked with divinylbenzene and with pendant methyleneaminodiacetic acid groups and (b) which have a crosslinked polyacrylamide or polymethacrylamide matrix with related groups. This second type of resin is described in German Offenlegungsschrift No. 2818921, the contents of which are herein incorporated by reference.

The preferred method of use of the complexes of the invention for contacting substrate with enzyme is downward flow of the substrate with the complex in a packed column, as normally practised in ion-exchange.

However, the reaction can be performed by upward flow in a column or by agitation in a batch vessel followed by separation of the resin by filtration. The latter two methods do not give such effective contact between substrate and enzyme and therefore give less efficient conversion.

The metals which can be used in the invention are generally transition metals such as titanium, tin, zirconium, vanadium or iron. Similarly, the enzymes mentioned above with regard to the experiments using nylon, glass or cellulose can be employed. In more general terms, metals having high stability constants with aminocarboxylic acid chelating agents such as EDTA as shown in the tables of stability constants issued as Special Publications 6, 17 and 25 by the Chemical Society, London are suitable. In the same way suitable enzymes for use in this method are not limited to the specific examples given in the introduction.

This invention is of use in one of the stages for the conversion of starch into fructose. This conversion is commercially important because fructose is much sweeter than sucrose and sources of starch are much cheaper than the sugar beet and sugar cane from which sucrose is manufactured. The conversion of starch into fructose occurs in three stages:

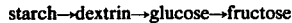

starch→dextrin→glucose→fructose

It is known to convert glucose to fructose successfully by the use of insolubilised forms of glucose isomerase. The present invention provides the possibility of converting dextrin to glucose using an insolubilised form of the relevant enzyme i.e. amyloglycosidase, with the advantage that the process can be conducted continuously.

The enzyme complexes of this invention may be prepared by the following procedure: A chelating resin is washed free of impurities and then treated in conventional manner with an aqueous solution of heavy metal ions e.g. ferric chloride until all available positions in the resin are judged to be occupied by chelated ferric iron. The resin is then washed free of electrolyte. A solution of the appropriate enzyme is now passed through the resin holding chelated metal until the maximum attachment of enzyme is achieved. The degree of attachment can be measured experimentally by washing the resin free of unlinked enzyme and then measuring its activity. When maximum attachment is reached, the resin is washed free of the extra enzyme solution with pure water. By using excess heavy metal ion followed by washing, consideration of the resin capacity is rendered unimportant.

By passing a solution of dextrin through a column of the resin, or otherwise bringing the solution into contact with the resin, conversion to glucose can be shown to occur by conventional analysis with Fehling's solution.

Consideration has been given to the question of the form of the chelate resin for most effective reaction and it has been found that the macroporous matrix form described in ion-exchange technology is the most suitable, allowing greater uptake of enzyme and access of dextrin in solution to the enzyme.

Four resins have been tested by preparing the ferric chelate of the resin using a ferric chloride solution under highly acidic conditions, followed by washing with demineralised water. The first resin is Amberlite XE-318, a macroporous polystyrene diacetic resin (Resin A). The second, third and fourth resins (Resins B, C and D) are polyacrylate resins with diaminoacetic acid groups, and are those of Examples 1, 2 and 3, respectively, of the said German OLS and are repeated in Examples 7 to 9 below. B and C are slightly macroporous whereas D is highly macroporous.

In the various experiments described below, the dextrin used was supplied as Dextrin BDH Pure, dissolved in water at the concentration specified. The amyloglucosidase enzyme was supplied as Glaxo Agidex 3800. The process works satisfactorily with other sources of these materials. Any efficiencies quoted however related to these materials for conformity in comparison. Determinations of conversion were made by the use of Fehling's solution by the standard techniques.

Three different methods were tried in relation to the attachment of the enzyme to the resin metal chelate.

(i) In columns, room temperature

Through 20 ml Fe-chelate in a burette column with 12 cm bed depth, 50 mls of enzyme/mixed bed water (ratio 1:4), were passed within 2 hours. The resin was rinsed with 10 BV mixed bed water.

(ii) In Beakers at Room temperature 20 mls of Fe-chelate were contacted with 50 mls of enzyme/mixed bed water (ratio 1:4) and left standing in a beaker for 5 days at room temperature. The resin was then transferred to a column and rinsed with 10 BV mixed bed water.

(iii) In Beakers at 40° C.

20 mls of Fe-chelate were contacted with 50 mls enzyme/mixed bed water (ratio 1:4) and left standing in a beaker in a water bath at 40° C. for 18 hours. The resin was transferred to a column and rinsed with 10 BV mixed water.

From preliminary results of the conversions obtained by these methods the procedure (i) was preferred and was adopted as the basis of further tests.

Three different methods were tried for the conversion of dextrin to glucose. The Fe-enzyme chelates prepared according to the above methods were submitted to the following experiments using 10% dextrin (BDH pure, insolubles 0.71 g/l).

(iv) In columns at room temperature

Through 20 mls of Fe-enzyme chelate in burette column bed depth 12 cm (or 22 cm) 100 mls of 10% dextrin were passed within 2 hours. 100 ml effluent (dilution factor 0.9) were collected in a volumetric flask. The refractive index was measured to find solid contents. Percent conversion was determined. Conversion: Resin A 60%, B 42%, C 48%, D 45%.

(v) In columns at 40° C.

Through 20 mls Fe-enzyme chelate, bed depth 12 cm, 100 mls of 10% dextrin were passed within 2 hours at 40° C. 100 mls effluent (dilution factor 0.9) were collected and analysed. Conversion: Resin A 58%, B 33%.

(vi) In Beakers at Room temperature 20 ml of Fe-enzyme chelate were placed in a flask, the excess water was sucked off and 100 ml of 10% dextrin were added and left standing stoppered for 65 hours. Refractive index was measured to determined solid contents. The liquid (dilution factor 0.9) was analysed for glucose. Conversion: Resin A 59%, B 40%, C 45%, D 68%.

Three examples of the process are now given each dealing specifically with the three stages covering preparation of iron chelate, fixation of enzyme and conversion of dextrin to glucose.

EXAMPLE 1

Formation of the Ferric Chelate Resin

Resin A was converted to the hydrochloride form using 50 BV 1 N HCl at a flow rate of 0.5 BV per minute and rinsed with mixed bed water to pH>4.0. This was followed by at least 50 BV FeCl$_3$ solution (1.6 Fe$^{3+}$/l) at a flow rate of 0.25 BV per minute and a definite colour change to chocolate brown of the resin and a decrease in volume was observed. The resin was rinsed with mixed bed water to pH>4.0. To confirm that iron had been taken up by the resin, a small rinsed sample was ashed, and inspected under the microscope. The reddish-brown colour of the residue clearly indicated Fe$_2$O$_3$ and the reaction with NH$_4$SCN was positive when the residue was dissolved in HCl. The Fe-resin chelate was left in contact with mixed bed water for 24 hours and the pH was measured but it remained unchanged.

EXAMPLE 2

Enzyme Fixation

The following method of enzyme fixation produced highest conversion (up to 60%) to glucose using BDH pure dextrin. 20 mls Fe$^{3+}$-resin chelate are placed in a 100 ml beaker with 10 ml Glaxo Agidex 3800 and 40 mls mixed bed water and left standing in a water bath at 40° C. for 18 hours. The resin is transferred to a column and rinsed with 10 BV of mixed bed water till free of excess enzyme.

EXAMPLE 3

Conversion of Dextrin to Glucose

Through 20 mls enzyme-Fe-resin chelate in a column 100 mls 10% w/v dextrin solution were passed within 2 hours. The effluent was collected in a 100 ml volumetric flask (dilution factor 0.9) and analysed for dextrose. The conversion was 70%.

EXAMPLES 4 to 6

The processes of Examples 1 to 3 were satisfactorily repeated with comparable results, using, respectively, resins B, C and D in place of Resin A.

In addition to the discovery of the complexes described above, it has been discovered that metals chelated by chelating resins have utility as plant nutrients.

Plants are dependent on the presence of a large number of metals in the soil for healthy growth, or even survival. Metals such as sodium, potassium, calcium and magnesium are present in all soils at all times in major proportions, though extra calcium is frequently added by liming the soil. These materials are present in all vegetable life in major proportions. In addition, however, there are a number of metals which occur and are used by the plants in small proportions and are therefore called "trace metals". Examples of such metals are iron, zinc, copper, manganese and molybdenum. If these trace elements are not available to the plant in sufficient quantity according to their needs faulty growth results which, in extreme cases, can be fatal to the plant and, in less extreme cases, result in, for example, very poor crops. In some cases the metal in question may actually be present in the soil but may be unavailable to the plant owing to the presence of other ingredients of the soil.

In the simplest cases the deficiency is remedied by the application of the metal as a simple salt. This may be done by application to the soil, either by spreading the salt on the surface, digging it into the soil, or spraying a salt solution onto the soil. These processes may be combined with the application of manures etc. where this is convenient and there are no unwanted interactions. Alternatively, simple salts of the trace metals may be directly applied to the plant as foliar sprays. This can be more economical than application to the soil where much of the metal supplied may be lost by drainage. However, the leaves may be sufficiently water-repellent to make this method unsatisfactory.

Trace metals are also applied to soil in the form of glass frits containing the appropriate metal. The glass weathers with time and releases the metal in the same way that natural rocks whether and renew the metal content of the soil.

All the above methods suffer from the problem that the metal may not be effective because the composition of the soil may precipitate the metal in a form unavailable to the plant or because excessive proportions of other metals make the concentration of the metal required by the plant ineffective.

To overcome these problems, trace metals have been applied agriculturally as water-soluble chelates since the early 1950's. The first material so used was EDTA (ethylenediaminetetraacetic acid) and this is still used in appropriate cases. Other soluble chelating agents have also been used where these have proved more effective than EDTA in the particular circumstances. These other materials have also been essentially aminocarboxylic acids but also containing other groups. The types of soluble chelating agents used and the agricultural work on this method in the most formative years is described in "The Sequestration of Metals" by R. L. Smith, Chapman & Hall Limited, London, 1959; while the developments of techniques and examples of such use has been most fully covered by various publications of Professor Arthur Wallace, University of California, Los Angeles. Metals are transported within the plants as chelates of natural aminocarboxylic acids which actually hold the metals less strongly then the synthetic aminocarboxylic acids used as suppliers. How the metals are detached from these synthetic agents of greater holding power has not yet been satisfactorily explained.

Conventional ion-exchange resins have been used to supply plant nutrients, including trace metals, in hydroponic or artificial horticulture systems. They have not been appropriate for open field culture or any other system subject to drainage as the counter cations and counter anions held by the resin are readily displaced by cations and anions dissolved in water in the soil. Thus in open culture, as opposed to hydroponics, trace metals so supplied have no advantage over the simple salts referred to above.

The use of chelated trace metals has been of great value. Their use has however been subject to great inefficiency in regard to the proportion of the metal supplied to the soil with respect to the amount of that metal which enters the vegetation for which it is intended. A figure such as 10% actual usage has been accepted as all that can be expected. The remainder is lost, presumably owing to drainage. In cases of excessive passage of water through the soil as much as 95% of the metal supplied may be lost. The treatment must thus be regularly repeated at intervals which depend on circumstances and the characteristics of the plant.

According to a second aspect of this invention, an agricultural composition comprises a complex of an agriculturally acceptable trace metal chelated by a chelating resin and an agriculturally acceptable dispersible carrier or diluent. An agricultural method according to the invention comprises applying a complex as defined above to a locus where a trace metal is required.

Any of the chelating resins decribed above may be used in this invention. The invention avoids many of the disadvantages associated with resin compositions since if a trace metal, for example manganese, is taken up on an ion-exchange resin it is readily displaced by calcium or magnesium, and in a greater concentration over a longer time by sodium or potassium, if placed in the soil. In the case of a chelating resin with pendant aminocarboxylic acid groups sodium and potassium are not chelated in any circumstances while calcium and magnesium are so relatively weakly held that they cannot displace chelated manganese. Thus manganese will not be lost in the soil from a chelating resin where it would be lost from an ion-exchange resin. This applies to all the trace metals where deficiency is undesirable. It is to be noted that boron is excluded from the scope of this invention since though agricultural literature frequently refers to it as a metal it is not a true metal and does not form chelates in the manner of true metals.

It is an advantage of this invention that the metal is fixed in position until released by local action. Therefore is does not migrate in the soil and so move only fortuitously towards roots. It must be placed in the vicinity of roots, by any appropriate method. For example, in transplanting a new tree from the nursery to its permanent site the novel composition is mixed with the soil surrounding the roots. With the correct quantity it should last the useful life of, say, a fruit tree. Where smaller plants are grown in rows then replanting or growth from seeds or shoots can be conducted on marked rows and only the soil in these rows need be enriched, to a useful depth. In the case of an existing tree where the soil cannot be disturbed or the roots exposed then suitable drillings are made through the soil where roots exist and a plug of the novel composition is inserted in the bore hole.

Roots do not grow fortuitously or haphazardly. Their growth depends on the varying nutritive value of the local soil. At points where existing roots have detected and used a nutrient or water then the roots proliferate in this vicinity and are meagre or absent in barren regions. Thus once the roots have made contact with a zone containing the composition of the invention they will multiply in that area. It is thought that roots can exude and reabsorb fluids which sense the presence of nutrients and can carry materials as trace metals into the root system.

The root ends must come into contact with the metal. It is preferred that the matrix of the resin is macroporous or macroreticular so that there are the largest possible pathways through the resin into which the finest root filaments can penetrate reaching the maximum number of sites. To achieve the maximum strength and long life of the resin it is preferred that it should be in bead form.

All organic materials are to some degree biodegradeable. We prefer that the matrix should be of low biodegradeability as the essence of the use of the novel compositions is their long life. However, there may be cases where greater biodegradeability is advantageous, and the resin can be chosen accordingly.

The compositions of the invention may comprise a finely divided solid as the carrier, and suitable carriers for agricultural purposes are known.

While the use of soluble chelates is well known and the advantages of an insoluble form have been already explained experimental work has been carried out in order to show that the plant can actually use the metal so held. The most difficult use of chelated metal in plant nutrition is in the correction of iron deficiency in calcareous, and thus alkaline, soil. The difficulties in effectively assisting plants under these conditions has been the subject of extensive studies on a very large scale.

The condition of a plant resultant on various treatments for metal deficiency may be judged by leaf colour, the content of the metal in the foliage by chemical analysis, and the weight of the plant grown under condition of the treatment in comparison to the growth in its absence. Leaf appearance is useful in quick assessment but is basically subjective in nature and cannot be rendered quantitatively. The metal content of the leaves by analysis of ashed samples might be expected to be the most important criterion of success. Unfortunately, however, it is well known that there is not necessarily any undoubted correlation between total metal by such chemical analysis and useful metal content in the plant, and it would appear that various metals can be present in plant leaves in forms which are not useful to plant growth. The most important criterion is the plant growth itself, measureable quantitatively by the average plant weight attained under varied conditions.

The figures in Table I below show that the presence of chelate resin in ferric form invariably gives rise to a notable increase in plant weight and shows that the plant can extract the metal bound to insoluble chelating resins and make profitable use of the metal so provided.

Because the Fe chelate resin is placed in the vicinity of each seed and is not distributed throughout the whole mass to the soil in each container it is not possible to express the additions as percentages of the total soil.

The resins used in the tests reported in Table I were those defined above as resins A and B, and also Dowex Chelating Resin A1 (referred to as Resin E) and Mitsubishi Resin CR10 (referred to as Resin F). A control experiment (plant no. 1) was also carried out.

Table I

| | Leaf yields of soya beans grown in calcareous loam soil | | |
|---|---|---|---|
| Plant number | Leaf yield (mg/plant) | Resin Quantity(g) | Resin Complex |
| 1 | 197 | 0 | — |
| 2 | 273 | 0.5 | Fe Resin A |
| 3 | 246 | 1.0 | Fe Resin A |
| 4 | 277 | 5.0 | Fe Resin A |
| 5 | 315 | 0.5 | Fe Resin E |
| 6 | 293 | 1.0 | Fe Resin E |
| 7 | 323 | 5.0 | Fe Resin E |
| 8 | 290 | 0.5 | Fe Resin F |
| 9 | 306 | 1.0 | Fe Resin F |
| 10 | 331 | 5.0 | Fe Resin F |
| 11 | 282 | 0.5 | Fe Resin B |
| 12 | 255 | 1.0 | Fe Resin B |
| 13 | 262 | 5.0 | Fe Resin B |

Comparable results to those given in Table 1 can be achieved by replacing Resin B by either Resins C and D or by Resin G, another novel resin within the terms of the said copending application. Preparations of each of Resins B, C, D and G are given, respectively, in the following Examples which are reproduced from the given German OLS.

EXAMPLE 7

Damp crosslinked (3% divinylbenzene) polyethylacrylate beads of 0.3 to 1.0 mm diameter (200 g) were suspended in 1200 g of diethylenetriamine and heated at 175° C. for 20 hours. The water present on the beads and the ethanol formed during the reaction as a by-product were allowed to distil off from the vessel. After cooling excess amine was filtered off and the resin washed with water. The characteristics of this intermediate were: swelling in water 1.64 g water/1 g dry resin; dry weight capacity 7.32 meq/1 dry resin.

To 796 g of chloroacetic acid dissolved in the minimum of water, 533 g of a 63% w/w solution of sodium hydroxide were added. The temperature was kept below 40° C. and the pH below 9.

To 2000 g of this solution was added 673 g of surface dry resin (approx. 260 g dry resin) and the mix was heated to 100° C. Over 5 hours, 240 g of sodium hydroxide were added dropwise as a 5% solution, the pH being kept below 9. After a further 1 hour at 100° C. the resin was washed with a limited quantity of water.

The resin was tested as follows:

A solution containing 1000 ppm Ca and 100 ppm Zn (both as chloride salts) was adjusted to a pH of 4.5. This solution was passed through a 10 ml column of the resin (in the sodium form) at the rate of 12 bed volumes per hour and the effluent was collected and analysed. The run was terminated at 2 ppm Zn breakthrough. Regeneration was carried out with N hydrochloric acid at 3 bed volumes per hour. 10 bed volumes gave complete elution.

The resin capacity for zinc in the presence of 10 times excess of calcium ion was 1.44 meq/g dry resin. A commercial chelating resin based on polystyrene structure gave a capacity 1.08 meq/1 g dry resin under identical experimental conditions.

EXAMPLE 8

Damp crosslinked (7% divinylbenzene) polyethyl acrylate heads containing 30% v/v heptane during their preparation of 0.3 to 1.0 mm diameter (200 g) were suspended in 1000 g diethylenetriamine and heated at 175° C., for 20 hours. The water and heptane present and the ethanol formed during the reaction as a by-product were allowed to distil off from the vessel. After cooling excess amine was filtered off and the resin washed with water. The characteristics of this intermediate were: swelling in water 1.61 g water/1 g dry resin; dry weight capacity 7.07 meq/1 g dry resin.

To 682 g sodium chloroacetate, dissolved in 400 ml water, 470 g of surface dry resin (approx. 180 g dry resin) were added, and the mix was heated to 100° C. Over 7 hours 166 g sodium hydroxide were added dropwise as a 5% w/v solution in water, the pH being kept below 9. After a further 1 hour at 100° C., the resin was filtered and washed with a limited quantity of water.

The characteristics of this chelating resin were: swelling in water 1.25 g water/1 g dry resin; $Cu^{++}$ capacity (total) 4.70 meq/g. The resin was slightly macroporous.

EXAMPLE 9

Damp crosslinked (2.5% divinylbenzene) polyethylacrylate beads of 0.3 to 1.0 mm diameter (200 g) were suspended in 1000 g ethylenediamine and heated at 117° C. for 20 hours. The water present in the beads and the ethanol formed during the reaction as a by-product were allowed to distil off from the vessel. After cooling excess amine was filtered off and the resin washed with water. The characteristics of this intermediate were: swelling in water 2.90 g water/1 g dry resin; dry weight capacity 5.47 meq/1 g dry resin.

To 900 g sodium chloroacetate dissolved in 520 ml water, 890 g surface dry resin (approx. 230 g dry resin) were added, and the mix was heated to 100° C. Over 4 hours 220 g sodium hydroxide were added drop-wise as a 5% solution, the pH being kept below 9. After a further 1 hour at 100° C. the resin was filtered and washed with a limited quantity of water.

The characteristics of this chelating resin were: swelling in water 1.90 g water/1 g dry resin, $Cu^{++}$ capacity (total) 5.42 meq/1 g dry resin.

EXAMPLE 10

Dry crosslinked polyacrylonitrile beads containing 6% divinylbenzene and 5% isoprene of 0.3 to 1.0 mm diameter (200 g) were suspended in 700 g diethylenetriamine containing 50 g water and heated at 150° C. in a pressure vessel for 20 hours. After cooling excess amine was filtered off and the resin washed with water. The characteristics of this intermediate were: swelling in water 1.12 g water/1 g dry resin; dry weight capacity 6.46 meq/1 g dry resin.

To 950 g sodium chloroacetate, dissolved in 600 ml water, 560 g of surface dry resin (approx. 270 g dry resin) were added, and the mixture was heated to 100° C. Over 10 hours 231 g sodium hydroxide were added dropwise as a 5% w/v solution in water, the pH being kept below 9. After a further 2 hours at 100° C., the resin was filtered and washed with a limited quantity of water.

The characteristics of the chelating resin were: swelling/water 0.73 g water/1 g dry resin, $Cu^{++}$ capacity (total) 3.30 meq/g resin.

I claim:

1. An enzymatically active enzyme-support complex comprising a resin having pendant chelating groups, a metal, and an enzyme having activity independent of the presence of the metal and the chelating resin, wherein the metal is chelated by both the chelating groups of the resin and the enzyme through coordinate bonds such that there is no localized charge on the metal.

2. The complex of claim 1 wherein the metal is iron.

3. The complex of claim 1 wherein the resin has pendant chelating groups selected from methyleneaminoacetic acid and methylenediaminoacetic acid groups.

4. The complex of claim 1 wherein the resin is based on crosslinked polystyrene.

5. The complex of claim 1 wherein the resin is based on a crosslinked polymer selected from polyacrylamides and polymethacrylamides.

6. The complex of claim 1 wherein the enzyme is amyloglucosidase.

* * * * *